United States Patent [19]
Graef et al.

[11] Patent Number: 5,399,240
[45] Date of Patent: * Mar. 21, 1995

[54] CROSSLINKED CELLULOSE PRODUCTS AND METHOD FOR THEIR PREPARATION

[75] Inventors: Peter A. Graef, Tacoma; Frank R. Hunter, Bellevue, both of Wash.

[73] Assignee: Weyerhaeuser Company, Tacoma, Wash.

[*] Notice: The portion of the term of this patent subsequent to Jul. 6, 2010 has been disclaimed.

[21] Appl. No.: 87,186

[22] Filed: Jul. 2, 1993

Related U.S. Application Data

[63] Continuation of Ser. No. 395,208, Aug. 17, 1989, Pat. No. 5,225,047, which is a continuation-in-part of Ser. No. 140,922, Dec. 28, 1987, abandoned, which is a continuation-in-part of Ser. No. 4,729, Jan. 20, 1987, abandoned.

[51] Int. Cl.$^6$ .............................................. D21H 11/20
[52] U.S. Cl. .......................................... 162/9; 8/116.1; 8/116.4; 8/184; 8/195; 162/158; 162/157.6; 162/182
[58] Field of Search ................ 162/9, 157.6, 158, 182; 8/716.4, 184, 195, 116.1; 536/56; 604/375

[56] References Cited

U.S. PATENT DOCUMENTS

| | | | |
|---|---|---|---|
| 2,285,490 | 6/1942 | Broderick | 117/157 |
| 3,069,311 | 12/1962 | Harpham et al. | 162/146 |
| 3,224,926 | 12/1965 | Bernardin | 162/146 |
| 3,395,708 | 8/1968 | Hervey et al. | 128/284 |
| 3,434,918 | 3/1969 | Bernardin | 162/111 |
| 3,440,135 | 4/1969 | Chung | 162/8 |
| 3,554,862 | 1/1971 | Hervey et al. | 162/158 |
| 3,658,613 | 4/1972 | Steiger | 8/116.4 |
| 3,677,886 | 7/1972 | Forssblad et al. | 162/72 |
| 3,700,549 | 10/1972 | Croon et al. | 162/157 C |
| 3,755,220 | 8/1973 | Freimark et al. | 260/17.3 |
| 3,819,470 | 6/1974 | Shaw | 162/157.6 |
| 3,844,880 | 10/1974 | Meisel, Jr. et al. | 162/169 |
| 3,932,209 | 1/1976 | Chatterjee | 162/157.6 |
| 4,035,147 | 7/1977 | Sangenis et al. | 162/157.6 |
| 4,144,122 | 3/1979 | Emanuelsson et al. | 162/158 |
| 4,204,054 | 5/1980 | Lesas et al. | 536/56 |
| 4,303,471 | 12/1981 | Laursen | 162/158 |
| 4,351,699 | 9/1982 | Osborn, III | 162/112 |
| 4,476,323 | 10/1984 | Hellsten et al. | 564/294 |
| 5,139,530 | 8/1992 | Blanchard et al. | 8/125 |
| 5,255,047 | 7/1993 | Graef et al. | 162/9 |

FOREIGN PATENT DOCUMENTS

| | | |
|---|---|---|
| 806352 | 2/1969 | Canada . |
| 813616 | 5/1969 | Canada . |
| 1259521 | 1/1972 | United Kingdom . |

OTHER PUBLICATIONS

Gagliardi, D. D. and F. B. Shippe, Crosslinking of cellulose with polycarboxylic acids. American Dystuff Reporter, Apr. 15, 1963, pp. 74–77.

Tesoro, Guiliana C. and John J. Willardc, Crosslinked cellulose, in Cellulose and cellulose derivatives, N. M. Bikales and L. Segal, eds., Part V, Wiley-Interscience, New York (1961), pp. 835–875.

*Primary Examiner*—Peter Chin

[57] ABSTRACT

The invention is a method of making a wet formed, sheeted, readily reslurriable sheeted crosslinked cellulose and the products made by the method. Crosslinked wood pulp fibers tend to be quite brittle. If crosslinked while in sheeted form, the sheets cannot be readily defibered, either in a wet or dry state, without serious fiber degradation. The sheet products of the present invention can be easily redispersed or repulped in water without significant fiber breakage. The present products are made by including within the sheet, while still in wet form, a debonding or softening agent which is preferably added before the latent crosslinking reactant. Most preferably the debonder is added prior to the headbox of a paper machine and the crosslinking reactant is applied near the end of the forming wire or at the press section. The treated sheet is dried conventionally. Crosslinking may occur entirely during drying or during a period of additional heating, usually at a temperature in excess of 100° C. for a short period of time. Conventional debonding agents and crosslinking reactants are suitable. The softening agent apparently reduces or prevents adhesive bonding between adjacent fibers caused by polymer formation external to the fibers under reaction conditions.

25 Claims, No Drawings

CROSSLINKED CELLULOSE PRODUCTS AND METHOD FOR THEIR PREPARATION

This is a continuation of application Ser. No. 07/395,208, filed Aug. 17, 1989, now U.S. Pat. No. 5,225,047, which is a continuation-in-part of application Ser. No. 140,922, filed Dec. 28, 1987, abandoned, which was a continuation-in-part of application Ser. No. 004,729, filed Jan. 20, 1987, abandoned.

BACKGROUND OF THE INVENTION

The present invention is directed to a method of making a sheeted crosslinked cellulose and the product resulting from the process. The invention is especially directed toward a crosslinked cellulose sheet which can later be easily reslurried in water without excessive fiber breakage.

Crosslinked cellulose products have been described in the chemical literature for many years. These products are normally made by reacting a material, ususally bifunctional, that will tie together hydroxyl groups on neighboring cellulose chains. Formaldehyde and various derivatives of urea have been the crosslinking agents which have received the greatest study. However, many other materials which have actual or latent bifunctional reactive groups have also been reported.

Crosslinked celluloses are of great commercial importance in the textile industry where they are widely used for the production of wash-and-wear and other wrinkle-resistant types of fabrics. Crosslinked cellulose fluff has also been described for use in disposable absorbent products such as diapers. Here advantage is taken of the fact that crosslinked fibers are normally stiffer than their untreated counterparts. The fluff products formed from these fibers are of Somewhat lower density (or greater bulk) and tend to hold retained liquid better under compressive forces encountered during use of the product.

While the advantages contributed to disposable absorbent products by crosslinked cellulose fibers are real, products using these crosslinked fibers have never become commercially important. This is apparently because of the difficulty of making a sheeted crosslinked fiber product that can be later refiberized at the point of use without creation of an excessive amount of fines. Unfortunately, crosslinking also results in considerable fiber embrittlement. Additionally, most of the crosslinking agents which have been used serve to give both chemical and physical bonding between adjacent fibers in the sheets. This, in addition to the increased fiber brittleness, has made mechanical wet or dry defiberization of sheeted crosslinked pulps impractical. In an effort to overcome this problem, various workers have considered treating sheeted pulp with a latent crosslinking material, fluffing, and then carrying out the crosslinking reaction by heating the cellulose fluff. An example of this is seen in Bernardin, U.S. Pat. No. 3,224,926. Van Haaften, Canadian Patent 806,352 treats loose fibers with a crosslinking material and catalyst. These moist fibers are then expanded into a loose fluffy condition and cured.

The stiffness of crosslinked cellulose fibers can add desirable properties to certain sheeted pulp products. Here it is typical to use only a portion of crosslinked fibers in the ultimate product. Attempts to do this have encountered the same problems mentioned earlier. If a product is crosslinked in sheeted form, it becomes very difficult to redisperse without serious fiber breakage by normal wet repulping processes employed in paper mills. As noted before, there are two apparent reasons for this. The strength of a sheeted cellulose product is developed in part by mechanical entanglement of the fibers but, much more so, by hydrogen bonding in those areas where fibers overlap are in intimate contact with each other. This hydrogen bonding develops only when the fibers are dry. In a crosslinked sheeted product, when the crosslinking reaction is normally carried out by heating after the sheet has been fully dried, two phenomena can occur. One of these is interfiber crosslinking. The reaction occurs in areas of intimate fiber-to-fiber contact and serves to chemically bind the fibers together. Perhaps of even greater importance, many of the crosslinking materials used also form thermosetting adhesives under the heated conditions used in the crosslinking reaction. Scanning electron micrographs of heated dimethylolurea treated fibers show many small spherical nodules of ureaformaldehyde resin on the surface and within the fiber lumen. These nodules serve to adhesively bond adjacent fibers so that it is very difficult to separate them under any conditions without considerable fiber breakage. Because the crosslinked fibers tend to be so brittle, the fibers themselves will often break leaving the bonded areas between adjacent fibers intact. There is a related side issue to this phenomenon. It is still an unresolved question as to how much of the crosslinking reaction is a surface phenomenon as opposed to an internal one.

Earlier workers in the field have also tried to deal with the problem of making a sheeted cellulose pulp product containing only a portion of crosslinked fibers. As one example, Bernardin, in U.S. Pat. No. 3,434,918, treats sheeted fiber with a crosslinking agent and catalyst. This is then wet aged to insolublize the crosslinker, so-called "wet fixation." This wet aged fiber is then redispersed before curing. The redispersed fiber can be mixed with untreated fiber and the mixture sheeted. The final product is then heat cured. In a variation of this process the same inventor, in Canadian Patent 813,616, heat cures crosslinked fibers as a fluff and then mixes this product with conventional papermaking fibers.

These mixtures of crosslinked fibers with untreated fibers are potentially useful for making products such as filter media, tissues, and towelling where high bulk and good water absorbency are desired without excessive stiffness in the product. Freimark et al, in U.S. Pat. No. 3,755,220, describe making a soft, high wet strength sheet, although this does not use crosslinked fibers. These inventors utilize well known debonders or softeners with cationic wet strength resins to gain an increase in the ratio of wet to dry tensile strength, usually without serious loss in absolute values of wet tensile strength. The debonder itself can be cationic or anionic and may be added to the papermaking stock prior to or following the addition of the wet strength resin.

In U.S. Pat. No. 4,204,054, Lesas et al describe spraying unsheeted bulk fibers with a solution of formaldehyde, formic acid and hydrochloric acid. These fibers are then immediately dispersed in a hot air stream at about 170°–200° C. for 1–20 seconds. This appears to give primarily surface area crosslinking without serious affect on fiber flexibility. The inventors note that 10–40% of these fibers can be mixed with conventional fibers to give a sheeted product with good flexibility and water absorbency.

Unfortunately, the problems encountered handling bulk fibers; i.e., those in individual loose form as opposed to a sheeted product, have been so great as to be commercially nearly insurmountable to the present time. The fiber must be dried by flash drying or some similar procedure where it is usually suspended in a hot air stream. The dried fiber is then baled or bagged. Because of the very short fiber length, compactly packaging a loose fiber form of wood pulp is technically very difficult and expensive. An alternative procedure, where the loose fibrous product might be prepared at the ultimate point of consumption, has been even more unattractive and has met with a wall of resistance by potential consumers.

The reader who might be interested in learning more detail of the chemistry of cellulose crosslinking can refer to any of the standard texts on cellulose. One resource which treats the subject quite thoroughly is by Tesoro and Willard in *Cellulose and Cellulose Derivatives*, Bikales and Segal, eds., Part V, Wiley-Interscience, New York (1971), pp. 835-875.

Reference was made to use of fiber debonders, also called sheet softeners in the earlier comments relating to U.S. Pat. No. 3,755,220. These materials can be generally classified as surfactants which are applied to the fiber while it is still wet, before any hydrogen bonding has occurred. Most typically they are cationic in nature, based on quaternary ammonium compounds which have one or more fatty substituents. Although not as commonly used, nonionic and anionic types are also commercially available. Frequently a combination of a cationic and nonionic type may be employed. These products are widely used within the pulp and paper industry and are commercially available from a number of suppliers. Similar products are used in the textile industry.

Debonders serve to make a softer sheet by virtue of the fatty portion of the molecule which interferes with the normal hydrogen bonding. They are quite commonly used in the manufacture of fluff pulps which will be later converted into absorbent products such as disposable diapers. The use of a debonder can reduce the energy required to produce a fluff to half or even less than that required for a nontreated pulp. This advantage is not obtained without a price, however. Many debonders tend to reduce water absorbency as a result of hydrophobicity caused by the same fatty long chain portion which gives the product its effectiveness. In order to overcome this problem, some manufacturers have formed adducts of ethylene or propylene oxide in order to make the products somewhat more hydrophilic. Those interested in the chemistry of debonders will find them widely described in the patent literature. The following list of U.S. patents provides a fair sampling, although it is not intended to be exhaustive: Hervey et al, U.S. Pat. Nos.3,395,708 and 3,554,862; Forssblad et al, U.S. Pat. No. 3,677,886; Emanuelsson et al, U.S. Pat. No. 4,144,122; Osborne, III, U.S. Pat. No. 4,351,699; and Hellsten et al, U.S. Pat. No. 4,476,323. All of the aforementioned patents describe cationic debonders. Laursen, in U.S. Pat. No. 4,303,471, describes what might be considered a representative nonanionic debonder.

U.S. Pat. No. 3,844,880 to Meisel, Jr. et al describes the use of deposition aid (generally cationic), an anionic resin emulsion, and a softening agent which are added sequentially to a pulp furnish to produce a soft product having high wet and dry tensile strength. The opposite situation; i.e., low wet tensile strength, is preferred for a pulp which is to be later reslurried for some other use.

Croon et al, in U.S. Pat. No. 3,700,549, describe a cellulose fiber product crosslinked with a polyhalide, polyepoxide, or epoxyhalide under strongly alkaline conditions. Epichlorohydrin is a preferred material. In their examples Croon et al teach the use of their treated fiber in absorbent products such as diapers and sanitary napkins. All of the crosslinking materials are insoluble in water. Croon et al teach three methods to overcome this problem. The first is the use of vigorous agitation to maintain the crosslinking agent in a fine droplet-size suspension. Second is the use of of a polar cosolvent such as acetone or dialkylsulfoxides. Third is the use of a neutral (in terms of being a nonreactant) water soluble salt such as magnesium chloride. In a variation of the first method a surfactant may be added to enhance the dispersion of the reactant phase. After reaction the resulting product must be exhaustively washed to remove the necessary high concentration of alkali and any unrelated crosslinking material, salts, or solvents. The method is suitable only for cellulosic products having a relatively high hemicellulose content. A serious deficiency is the need for subsequent disposal of the toxic materials washed from the reacted product. The Croon et al material would also be expected to have all other well known disadvantages incurred with trying to sheet a stiff, brittle crosslinked fiber.

To the knowledge of the present inventor, no one has ever before used a debonder with a cellulose pulp which is also treated with a crosslinking agent. One skilled in the art would not expect this to be an effective combination, i.e., they would expect the interfiber bonding propensities of the crosslinking agents to completely overpower any advantage in the reduction of wet or dry strength that might be contributed by the debonding agent.

SUMMARY OF THE INVENTION

The present invention is a method of making wet formed, sheeted crosslinked cellulose and the products produced thereby which can be easily reslurried to a free fiber condition without excessive fiber breakage. The method comprises including within the sheet while still wet a debonding agent and water soluble or water dispersable latent cellulose crosslinking agent. The sheet thus treated is dried and, during or after drying the crosslinking agent reacts with the cellulose. In the most preferred form of the invention, the debonding agent is added to an aqueous slurry of cellulose fibers prior to sheet formation and a latent crosslinking agent is added subsequent to sheet formation. This can be readily accomplished by spraying an aqueous solution or disperson of the crosslinking agent onto the sheet while it still on the forming wire or in the press section of the paper machine. However, it is within the scope of the invention to add both the debonding agent and the latent crosslinking agent to the wet sheet following sheet formation. In this ease it is preferable to add the debonding agent to the wet sheet prior to the addition of the latent crosslinking agent. The latent crosslinking agent should be added to sheeted cellulose while it is at a moisture content greater than about 10%, preferably greater than about 30%.

It is within the scope of the invention to use a debonding agent which may be either cationic, nonionic or anionic in nature.

The latent crosslinking agent may be selected from any of the following well known materials which serve this function. Preferred types are selected from urea derivatives such as methylolated urea, methylolated cyclic ureas, methylolated lower alkyl substituted cyclic ureas, dihydroxy cyclic ureas, lower alkyl substituted dihydroxy cyclic ureas, methylolated dihydroxy cyclic ureas, and mixtures of any of these types. A presently preferred latent crosslinking material is dimethyloldihydroxyethyleneurea (DMDHEU, 1,3-dihydroxymethyl-4,5-dihydroxy-2-imidazolidinone). This material is readily commercially available in a stable form. Other urea-based materials which are eminently suitable include dimethylol urea (DMU, Bis[N-hydroxymethyl)]urea), dihydroxyethyleneurea (DHEU, 4,5-dihydroxy-2-imidazolidinoe), dimethylolethylene urea (DMEU, 1,3-dihydroxymethyl-2-imidazolidinone, and 4,5-dihydroxy-1,3-dimethyl-2-imidazolidinone (DDI, dimethyldihydroxyethyleneurea).

In addition to those latent crosslinking agents based on urea, other materials that are suitable are polycarboxylic organic acids. Among these 1,2,3,4-butanetetracarboxylic acid is a presently preferred material.

All of the crosslinking agents just described may be reacted with the cellulose either during normal drying of the sheeted material or subsequent to this time by raising the dried sheet to an elevated temperature, preferably above 100° C.

A neutral or acidic catalyst may be included with the latent crosslinking agent to increase the reaction rate between the crosslinker and the cellulose. Acidic salts are particularly useful as catalysts when the urea-based materials are employed. These salts may typically be ammonium chloride or sulfate, aluminum chloride, magnesium chloride or mixtures of these or many other similar materials. Alkali metal salts of phosphorous-containing acids, such as sodium hexametaphosphate and sodium hypophosphite, with or without additional oxalic acid, are useful catalysts for 1,2,3,4-butane carboxylic acid.

The crosslinking agent is typically present in an amount in the range of 2–200 kg/t, preferably 20–100 kg/t, of cellulose fiber. Similarly, the debonding agent is generally present in an amount of about 0.1–20 kg/t, preferably 1–10 kg/t, of cellulose fiber.

A particular advantage of the new process is found in the lack of any need for washing the sheeted crosslinked product after the crosslinking reaction is completed.

It is an object of the present invention to provide a sheeted crosslinked cellulose product which can be readily reslurried in water to a free fiber condition without excessive fiber breakage or energy input.

It is a further object of the invention to provide a method of manufacturing such a product.

It is another object to provide a method and product as described which can be conveniently and readily made on conventional papermaking equipment.

It is yet another object to provide a product of the types described which can be readily redispersed in water and mixed with other types of fibers, which mixtures can be resheeted to give products having novel and useful properties.

These and many other objects will become readily apparent to those skilled in the art upon reading the following detailed description.

DESCRIPTION OF THE PREFERRED EMBODIMENTS

The sheeted crosslinked cellulose products of the present invention are intended for use as manufactured, or for remanufacture by a process that involves redispersing the product in water, usually for admixture with other fibers, followed by resheeting. It is not a primary goal or intention of the invention to produce sheeted products useful in processes that involve dry mechanical defibering, even though some species may perform satisfactorily under these conditions. The present invention provides a sheeted crosslinked cellulosic product that contributes good bulk and absorbency to a remanufactured sheet with little or no loss of fiber integrity or length during the remanufacturing process.

While the individual use of debonding agents and crosslinking reagents have been both known for some time in the pulp and paper industry, these have never before been used in combination in a sheeted pulp product, to the knowledge of the present inventor. It was totally unexpected that the debonders would continue to function as such after treatment of and reaction of the fibers with crosslinking materials. This is especially the case since many crosslinking agents will, at least to some extent, form polymers as a side reaction while reacting with the cellulose. In many cases these polymeric side reaction products serve as powerful adhesive materials. As one example, the efficiency of urea-based polymers as bonding agents for cellulosic materials is well known. Many of the precursors of these urea adhesives are the identical materials that are also highly effective cellulose crosslinking agents.

To the inventors best knowledge, any latent cellulose crosslinking composition is effective in the present invention. Those that can be reacted at relatively low temperatures in short periods of time during or after normal drying are preferred from a technical and economic standpoint. The urea-based crosslinking materials seem to fill this requirement well since their reaction speed can be greatly accelerated with small amounts of inexpensive acidic salt catalysts. Other classes of crosslinking agents can probably be similarly accelerated as well. No representation is made here that any of the processes described in the following examples have been optimized.

In similar manner, it appears that any class of debonding agent will be satisfactory, although there is some indication that cationic types may be superior to nonionic or anionic materials. Again, the systems reported here have not been optimized.

Cationic debonders are most usually based on quaternary ammonium salts having one or two lower alkyl substituents and one or two substituents that are or contain a fatty, relatively long chain hydrocarbon. Most of these fall into one of four general types as follows:

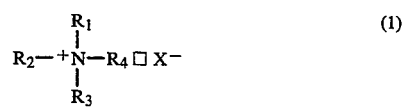

(1)

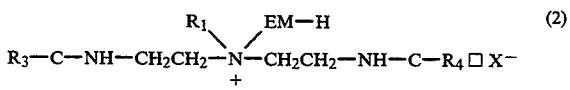

(2)

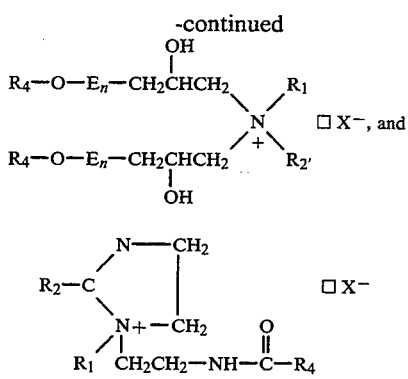

where $R_1$ and $R_2$ are methyl, ethyl, or hydroxyethyl, $R_3$ is a hydrogen having 1-40 carbon atoms, $R_4$ is a hydrocarbon having 10-40 carbon atoms, E is an oxyalkylene group having 2 or 3 carbon atoms, m is an integer from 1-20, n is an integer from 0-20, and X is Cl or $SO_4$, said hydrocarbon substituents being selected from linear and branched alkyl or alkenyl groups, and branched and linear alkyl and alkenyl substituted phenyl groups. Most typically $R_3$ will have from 1-22 carbon atoms and $R_4$ from 10-22.

Originally most debonders were Type 1 fattyalkyl di- or trimethyl ammonium compounds. These have now been superceded in many cases by the other types since they may induce an undesirable hydrophobicity.

The Type 2 debonders, diamidoamine types, are quite inexpensive and are widely used as fabric softeners.

Dialkyl alkoxylated quaternary ammonium compounds (Type 3) are widely used in making fluff pulps for disposable diapers since the polyethylene or propylene oxide chains give better hydrophylicity and cause less degradation of absorbency, especially when compared with Type 1 compositions.

The imidazoline materials that comprise Type 4 materials are somewhat newer materials. However, they are also now widely used.

Nonionic materials that can serve as debonders comprise a very large class of materials. Principal among them are adduct type reaction products of fatty aliphatic alcohols, fatty alkyl phenols and fatty aromatic and aliphatic acids with ethylene oxide, propylene oxide or mixtures of these two materials. Most typically the fatty portion is a hydrocarbon chain having at least 8, more typically 10-22, carbon atoms. Other useful nonionic debonders include partial fatty acid esters of polyvalent alcohols and their anhydrides wherein the alcohol or anhydride has 2-8 carbon atoms.

Anionic debonders also include a large class of materials, including many having surfactant properties. In general these are sulfated fats, fatty esters, or fatty alcohols. They also include fatty alkyl substituted aromatic sulfonic acids. The fatty substituent groups may have from 8-40 carbon atoms, more typically from 10-22 carbon atoms.

In the most preferred practice of the invention the debonder will be added to the cellulose fiber stock at some point before the headbox of the paper machine. When anionic or nonionic debonders are used it is normal practice to also use a cationic retention aid at the point of or immediately prior to their addition. Otherwise, they will have very poor substantivity to the cellulose fibers. It is within the scope of the invention to add both the softener and latent crosslinking agent after formation of the sheet. In this case it is not always necessary to use retention aids with nonionic or anionic debonders.

The following examples will illustrate the best modes presently known to the inventor for carrying out the present process and making the resulting products.

EXAMPLE 1

The following procedure was used to make laboratory handsheets for evaluation. A 25 g (dry weight) sample of unrefined cellulose pulp was reslurried in a Waring Blendor at about 2% consistency for 20 seconds. After 5 seconds of agitation, one of the commercially available softening agents was added to the blender in amounts ranging from 0% (for control samples) to 2% based on dry pulp. Most typical usage was about 0.5% (5 kg/t), on an as received basis. The reslurried, softener treated pulp was further diluted to a volume of about 6800 mL with water. This slurry was formed into a sheet on a standard 8×8 inch (203×203 mm) Noble and Wood laboratory sheet mold, using a 150 mesh stainless steel screen. The sheet was removed from the former and pressed between synthetic fiber felts so that the moisture content was reduced to about 50%.

The moist sheet prepared as above was then immersed into a bath containing a known concentration of a latent crosslinking agent and catalyst, if the latter component was used. After immersion the sheet picked up sufficient treating liquid so that its consistency was reduced to about 13.5%. It was again pressed between felts to about 50% fiber content. It can be readily calculated to show that the final pickup of latent crosslinking agent and catalyst, based on pulp, was about 84% of the concentration in the bath. The handsheet was then drum dried to about 5% moisture content.

Depending on the particular crosslinking agent and/or catalyst used, the crosslinking reaction with the cellulose occurred either during the drying step or in an oven curing stage following drying.

EXAMPLE 2

The bulk density of a crosslinked pulp sheet is dependent on a number of interacting factors: the physical nature of the cellulose, the type and amount of softener used, the type and amount of crosslinking agent and/or catalyst used, and the time and temperature of the crosslinking reaction. The effect of time-temperature relationship for one set of conditions can be seen in the following example using laboratory handsheet samples.

A bleached Douglas-fir kraft pulp was reslurried as described in Example 1 and treated with 0.5% as received of Berocell 584 softener. This material is a quaternary ammonium based softener believed to be principally a fatty substituted oxyalkylatedphenol dialkyl quaternary ammonium chloride (see the Type 3 quaternary formula noted earlier). This is compounded using 30% of the quaternary compound with 70% of a nonionic polyoxyalkylene composition. It is available from Berol Chemical Co., Reserve, Louisiana. After sheeting and pressing, the handsheets were treated with a 10%, as received basis, aqueous solution of Aerotex 900 latent crosslinking agent. Aerotex is a registered trademark of and is available from American Cyanamid Company, Wayne, New Jersey. It is believed to be a dimethyloldihydroxyethyleneurea product and is sold as an aqueous solution at about 45% solids concentration. For every 100 parts of the Arotex 900 solution, 30 parts by weight of Arotex Accelerator 9 catalyst solution were used. This is a 30% by weight solution of acidic salts believed to be aluminum and magnesium chlorides. Retention of the latent crosslinking agent, on a 100% solids basis, was calculated to be 3.78% of the dry cellulose present. The dried sheets were cured at 150° C. for 3 minutes.

In order to determine the reslurring and bulking properties of the treated fiber a 3.5 g, dry weight, sample was torn into small pieces and reslurried in about 2 L of water in a British Disintegrator. Agitation was continued until the slurry was smooth and free of obvious knots or fiber bundles. The number of revolutions to this point was counted and is an indicator of the ease with which the material can be redispersed. The slurry was then sheeted in a standard 6¼ in (159 mm) TAPPI sheet mold. After draining it was vacuum couched but was then drum dried without pressing. Bulk density was measured on the dried samples. High bulk values are generally an indication of high fiber stiffness. However, high bulk values cannot be obtained if there has been any significant amount of fiber breakage during reslurring. For this reason, bulk density is also strongly indicative of fiber length and of any fiber damage during reslurrying.

TABLE I

| | Control (Untreated) | Crosslinked Pulp | |
|---|---|---|---|
| | | No Debonder | Debonded |
| Disintegration Energy, revs. | 15,000 | 125,000 | 20,000 |
| Handsheet Bulk Density, cm³/g | 3.1 | 9.5 | 16.5 |

EXAMPLE 3

The reaction conditions; i.e., time, temperature, and catalyst concentration, between the potential crosslinking agent and the cellulose affect the bulking potential and ease of reslurrying of the sheeted product. A series of handsheets was made according to the procedures outlined in Examples 1 and 2. However, this time the amount of as received Arotex 900 in the treatment bath was varied in 5% steps between 0% and 20%, resulting in pickups by the fiber varying between 1.9 and ? .6%, as calculated on a dry materials basis. A constant weight ratio of 10:3 between as received crosslinker and catalyst was maintained for all samples. This ratio may be expressed as 5:1 on a dry solids basis. The resulting 203×203 mm Noble and Wood handsheets were resheeted as in Example 2 in the TAPPI sheet mold to obtain samples for bulk densities. Results were as follows:

TABLE II

Effect of Curing Conditions on Handsheet Bulk Density
TAPPI Handsheet Bulk Densities, cm³/g

| Crosslinker Solids Based on Pulp, % | Reaction Temperature | | | | | | | | |
|---|---|---|---|---|---|---|---|---|---|
| | 120° C. | | | 140° C. | | | 160° C. | | |
| | 1 min | 3 min | 5 min | 1 min | 3 min | 5 min | 1 min | 3 min | 5 min |
| 0 | | | | | 3.2 | | | | |
| 1.89 | 3.8 | 6.7 | 5.2 | 7.6 | 9.5 | 10.5 | 10.3 | 14.1 | 15.8 |
| 3.78 | 9.7 | 13.2 | 16.0 | 15.3 | 15.7 | 17.7 | 19.3 | 14.6 | 14.5 |
| 5.67 | 6.7 | 16.8 | 20.4 | 18.6 | 17.7 | 16.7 | 20.0 | 14.8 | 14.8 |
| 7.56 | 9.0 | 19.3 | 19.7 | 19.6 | 16.1 | 17.4 | 20.0 | — | — |

It is readily apparent that with the present crosslinker system, TAPPI sheet bulk density increased directly with increases in crosslinker usage, reaction time, and reaction temperature. However, little change was seen in sheet bulk with increase in reaction time from 3 to 6 minutes, especially at the two higher curing temperatures. Likewise, there does not appear to great advantage at reacting at the higher temperature of 160° C. compared with 140° C. In fact, at higher crosslinker usages the higher temperature may cause undesirable fiber embrittlement.

EXAMPLE 4

A series of samples was made using a 10% Arotex 900 bath treatment and comparing the Berol 584 softener, used in Examples 2 and 3, with a nonionic softener and a nonionic/cationic softener combination. The nonionic material was Triton X-100, a nonylphenol type. Triton is a registered trademark of and the product is available from Rohm and Haas Co., Philadelphia, Pennsylvania. The samples without softener and with the cationic softener were made as in Example 2. In the case where the nonionic softener by itself was used in combination with the crosslinking agent, both were included in the crosslinker bath and no softener was added prior to sheet formation. Estimated concentration of nonionic material solids incorporated into the final product, based on dry cellulose, is 0.8%. When the cationic/nonionic combination was used, the cationic was added as in Example 2, prior to sheeting, and the nonionic was included with the crosslinking agent as just described. In addition to sheet bulk density values, disintegration energy was estimated by noting the number of British Disintegrator revolutions necessary to give a uniform fiber dispersion without knots or fiber clumps. Results were obtained as shown in Table III.

TABLE III

| Sample | Disintegration Energy, revs | Handsheet Bulk Density, cm³/g |
|---|---|---|
| No debonder | 120,000 | 11.9 |
| Cationic debonder | 22,500 | 24.7 |
| Nonionic debonder | 62,500 | 16.9 |
| Cationic/nonionic | 62,500 | 18.4 |

The nonionic softener significantly improves ease of dispersibility and increases bulk value, However, it is not as effective here as the cationic debonder and, when used in combination under these conditions, reduces the effectiveness of the cationic material.

EXAMPLE 5

A major use of the products of the invention is expected to be in filtration medium. Here some portion of the crosslinked fiber would normally be repulped, blended with untreated fiber, and resheeted. A major contribution of the crosslinked fiber is porosity control and, in some eases, it can make higher porosities possible than can now be readily attained. One common measure of the expected behavior of a filter medium is air porosity. A number of test procedures are employed.

The particular one chosen is in part dependent on the expected air resistance of the sheet. The tests on the present product were conducted on sheets having a basis weight of 160+5 g/m² by measuring the pressure drop caused by an air flow of 0.085 m³/min.

Sheets were formed using 3.5 g, dry weight, of pulp dispersed in a British Disintegrator in about 2 L of water until a uniform slurry was produced. Sheets were formed in a standard laboratory British Sheet Mold, couched at 68.9 kPa, drum dried between blotters, and heated for 1.5 minutes at 150° C. to react the cellulose and crosslinker. Before testing sheets were conditioned to equilibrium at 50% RH at 23° C.

For the tests reported below in Table IV, Arotex 900 was used in bath concentrations of 1, 3, 5, 10, and 15% and the fiber was treated before sheeting with 0.5% Berocell 584 debonding agent.

TABLE IV

Bulk and Air Resistance of Crosslinked Fiber

| Crosslinker Solids Based on Pulp, % | Handsheet Bulk Density, cm³/g | Air Resistance Pressure Drop, mm |
|---|---|---|
| 0 | 3.7 | 37 |
| 0.38 | — | 19 |
| 1.13 | 8 | 4.3 |
| 1.89 | 10 | 3.0 |
| 3.78 | 21 | 0.5 |
| 5.67 | 23 | 0.5 |
| Untreated Control[1] | 5.5 | 3.3 |

[1]A commercially available prehydrolyzed, cold caustic extracted southern pine kraft pulp widely used in filter media.

The desirable air resistance properties contributed by the readily redispersible crosslinked cellulose pulp are immediately apparent.

EXAMPLE 6

Another expected major use of the products of the present invention is in tissues and toweling in order to maintain high bulk and softness with good water absorbency. To show the effectiveness of the crosslinked material, a sample was prepared as in Example 3 using a bath concentration of 15% Arotex 900. This resulted in a pickup of crosslinker solids based on dry pulp of about 5.7%. Varying amounts of this product were reslurried and added to fiber obtained by reslurrying two popular brands of toilet tissue. One of these, Tissue A, was a conventional hot drum dried product while the other, Tissue B, was originally dried using heated air passed through the tissue to maintain softness.

Sheets were formed in a standard laboratory British Sheet Mold as described in the previous example using 0.44 g, dry weight, of fiber to give a final sheet having a basis weight of about 24 g/m2. In addition to the bulk density value, softening efficiency of the crosslinked pulp in the ultimate sheet was estimated. This was calculated by taking the ratio (% increase in bulk density over a control sample) divided by (% treated pulp used in the sample). Results are given in the following table:

TABLE V

Addition of Crosslinked Pulp into Tissue Furnish

| Treated Pulp Used in Furnish, % | Tissue A | | Tissue B | |
|---|---|---|---|---|
| | Bulk, cm³/g | Efficiency | Bulk, cm³/g | Efficiency |
| 0 | 4.0 | — | 3.5 | — |
| 10 | 4.5 | 1.2 | 4.9 | 3.7 |
| 20 | 5.4 | 1.7 | 5.8 | 3.1 |
| 40 | 7.7 | 2.3 | 8.4 | 3.0 |
| 60 | 11.2 | 3.0 | 13.0 | 4.5 |

The effectiveness of the crosslinked pulp at increasing bulk is immediately apparent. It was unexpected that the bulking efficiency would increase as higher levels of crosslinked pulp were used.

EXAMPLE 7

In order to compare different cyclic urea compositions a supply of dihydroxyethyleneurea (DHEU) was prepared by reacting equimolar portions of glyoxal and urea, generally as taught in British Patent 717,287. This was compared with the Arotex 900 dimethyloldihydroxyethyleneurea (DMDHEU) used in the previous examples. Using 15% of each compound in respective treatment baths, samples were made up as described in Example 2. 30% of Arotex Accelerator 9 was used with the Arotex 900 in the treatment bath while 30% of a 10 g/L zinc nitrate solution was used with the DHEU. After drying, reaction times between the crosslinking agent and cellulose of 1-3 minutes were used at a temperature of 140° C. Table VI shows that nearly identical bulk values were obtained with the two compounds.

TABLE VI

| Reaction Time, min | Handsheet Bulk Density cm³/g | |
|---|---|---|
| | DMDHEU | DHEU |
| 1 | 25 | 24 |
| 3 | 28 | 29 |
| 5 | 26 | 25 |

The two compounds appear to be about equally effective and there appears to be no advantage for using longer reaction times.

EXAMPLE 8

The following tests were made to show the effectiveness of other generic classes of chemical crosslinking agents for cellulose.

A 20 g (oven dried weight) sample of never dried Northwest bleached kraft softwood pulp at 35% consistency was weighed out and placed in a British Disintegrator, made up to 2 L with deionized water, and agitated for 5 min at 600 rpm. The reslurried fiber was then dumped into an 8"×8" (203×203 mm) Noble and Wood laboratory sheet mold containing 4 L of deionized water. More water was added up to 2" below the top of the mold to give a total of about 6.3 L. A perforated stainless steel plate somewhat less than the cross sectional size of the sheet mold, with a 12" handle, was inserted into the sheet mold and moved up and down three times in rapid succession and 1 time slowly. The valve on the bottom of the sheet mold was opened and the stock drained through the screen. The pad of pulp remaining on the screen was removed, placed between synthetic fiber felts, and squeezed very gently through press rolls. The final weight of the pad was 65 g (45 g water and 20 g pulp).

A 1% solution of as received Berocell 541 (Berol Chemical Company, Reserve, Louisiana) was made up and sprayed onto both sides of the pulp pad (approximately equal distribution) to obtain an uptake of 1% softener based on OD pulp. After 3 min a 15% solution of maleic anhydride (MA) in water was sprayed onto the pulp pad in the same manner for a 15% (based on OD pulp) material uptake. The pad was then placed between 2 dry 8"×8" pulp blotters and fed through the drum dryer until the pad was completely dry. It was then transferred to a watch glass and placed in a 160° C. oven for 15 minutes. A 3.5 g sample was torn off the pad and reslurried in the British Disintegrator (using 2 L of deionized water) for 5 min at 600 rpm. The slurry was passed into a 6¼" TAPPI sheet mold and processed to a hand sheet. The pad was drum dried without pressing, conditioned at 50% RH and 23° C., and measured for bulk density.

In like manner, additional samples were treated with 1,2,3,4-butanetetracarboxylic acid (BTCA), 4,5-dihydroxyl-1,3-dimethyl-2-imidazolidinone (DDI), with and without softener. The samples made with DDI included 1% (based on pulp) of a mixed $AlCl_3 * MgCl_2$ catalyst. All samples were run in duplicate. Results are given in Table VII. Sheet formation was graded relatively as follows:

1—uniform good formation
2—fairly good formation without nits (undispersed fiber clumps)
3—fair formation with some knots or floes present
4—very poor formation with original sample not completely redispersed.

TABLE VII

Bulk Values Using Various Cellulose Crosslinking Agents

| Treatment | Bulk Value cm³/g | Relative Dispersibility |
|---|---|---|
| Untreated | 4.90 | 2 |
| 1% softener | 4.87 | 1 |
| 15% MA | 5.38 | 3 |
| 15% MA + 1% Softener | 6.51 | 1 |
| 15% DDI | 5.82 | 2 |
| 15% DDI + 1% Softener | 7.73 | 1 |
| 15% BTCA | 6.3(1) | 4 |
| 15% BTCA + 1% Softener | 10.17 | 1 |

(1)Best estimate attainable due to very poor formation

In all cases, except with glyoxal, the bulk value was improved when a softener was incorporated into the cellulose prior to addition and reaction of the crosslinking agent. Tests made under other conditions have shown glyoxal to be an effective material in the application. All of the softened samples reslurried more readily than those without the softener.

EXAMPLE 9

The work described in Example 2 was repeated in order to make a fiber length measurement study on reslurried sheets. One difference this time was an increase in the concentration of Arotex 900 from 10% to 15% on an as received basis in the treatment bath. A second difference was the use of 0.5% Varisoft 727 as the debonding material. Varisoft is a registered trademark of Sherex Chemical Company, Dublin, Ohio. Verisoft 727 is a formulated alkyl diamidoamine type quaternary compound in which the alkyl substituents are typically oleyl or tallow based. The composition contains about 30% quaternary material.

The higher concentration used here, as compared with Example 2, would be expected to increase the ultimate concentration of the latent crosslinking material in the cellulose fiber from about 3.8% to 5.7% and also to increase the brittleness of the crosslinked fibers. Fiber length determinations were made using a Kajanni Type FS-100 automatic fiber length analyzer, available from Kajanni Electronics Co., Kajanni, Finland. As before, the samples were dispersed in the British Disintegrator until smooth, knot free slurries were attained. Results are given below.

TABLE VIII

| | Control (Untreated) | Crosslinked pulp | |
|---|---|---|---|
| | | No Debonder | Debonded |
| Disintegration Energy, revs | 15,000 | 138,000 | 25,000 |
| Handsheet Bulk Density, cm³/g | 3.1 | 7.9 | 20.9 |
| Weighted Ave. Fiber Length, mm | 3.0 | 1.3 | 2.4 |

The debonded crosslinked pulp retained 80% of the fiber length of the control sample with very little more disintegration energy being required to redisperse the sheets in water. The crosslinked samples without debonder had only 43% of the average fiber length of the control samples. This major reduction is probably due to the very much higher energy required to obtain a smooth, knot-free fiber slurry.

EXAMPLE 10

A set of experiments was made to show the relative effectiveness of other types of quaternary debonding agents when used in conjunction with the Arotex 900 dimethyloldihydroxyethyleneurea (DMDHEU) latent crosslinking agent. The type numbers listed below refer to those noted earlier in the description of preferred embodiments.

Variquat and Adogen are registered trademarks of Sherex Chemical Company. Variquat 638 is described as a methyl bis(2-hydroxyethyl) coco ammonium chloride having 74–75% quaternary material. Adogen 471 is a tallow trimethyl ammonium chloride with 49–52% quaternary material. Varisoft 222–90% is a methyl his(-tallow amidoethyl) 2-hydroxyethyl ammonium methyl sulfate with 89–91% solids. Quaker 2006 is an imidazoline type debonder available from Quaker Chemical Co., Conshohocken, Pa.

TABLE IX

Effect of Quaternary Debonder Type with DMDHEU Crosslinking Agent

| | Type | Disintegration Energy, revs | Bulk Density, cm³/g |
|---|---|---|---|
| Variquat 638(1) | 1 | 125,000 | 10.5 |
| Adogen 471 | 1 | 30,000 | 14.6 |
| Verisoft 222-90% | 2 | 30,000 | 19.9 |
| Verisoft 727 | 2 | 30,000 | 18.3 |
| Quaker 2006 | 4 | 30,000 | 19.5 |

(1)This is a modified Type 1 material in that $R_2$ and $R_3$ are 2-hydroxyethyl or polyoxyethanol.

Representatives of all the general types of quaternary debonders worked well, although the modified Type 1 material does not seem as effective under the conditions used as the other materials.

EXAMPLE 11

Nonionic and anionic material additives are not substantive to cellulose fibers in an aqueous slurry unless the electrical charge on the fiber surface is made more compatible. This is normally done by adding one of the class of papermaking chemicals generally called retention aids prior to the addition of the nonionic or anionic composition. These are most typically cationic materials that are substantive to the fibers and make the surface charge more positive. When anionic or nonionic debonders are used in the present invention they can be added at the wet end, prior to sheeting, or after the sheet is formed. When wet end addition is chosen a cationic retention aid is normally required. If a shower over the forming wire or press section, or a pad bath, is used the retention aid is normally not necessary since most of the debonder remains with the water entrapped in the sheet.

A series of experiments was made to show disintegration energy and bulk values with the two modes of addition using cationic, anionic and nonionic debonding agents. For the wet end addition of the nonionic and anionic materials, 0.5% (5 kg/t) of the retention aid Reten 210 was added to the fiber slurry prior to the addition of the debonder. Reten is a registered trademark of Hercules, Inc., Wilmington, Delaware, for a very high molecular weight polyacrylamide having approximately 2–4 mol % cationic sites. No retention aid was used with the cationic material. The cationic debonder was Varisoft 727, described in Example 10; the nonionic material was Triton X-100, described in Example 4; and the anionic was a sodium linear alkyl sulfonate composition with 26.8% active material obtained from Chemithon Corp., Seattle, Washington. These were all used in dosages of 5 kg/t of the as received material. Those samples in which the debonder and latent crosslinking agent were added after sheet formation were prepared according to the procedure of Example 4, with the two materials being mixed in the same treating solution. All samples were made using 15 kg/t as received of Arotex 900 crosslinking agent in the treating bath. Relative dispersibility was evaluated by the criteria set forth in Example 8, with the exception that here the samples were retained in the British Disintegrator for a sufficient number of revolutions to obtain a relatively smooth slurry. Results were as follows.

TABLE X

Point of Addition of Debonding Agent

| Debonder Class | Point Addition | Disintegration Energy, revs | Bulk Density, cm³/g | Relative Dispersibility |
|---|---|---|---|---|
| Cationic | Wet End | 30,000 | 17.9 | 1 |
|  | Pad Bath | 30,000 | 18.3 | 1 |
| Nonionic | Wet End | 138,000 | 11.9 | 3 |
|  | Pad Bath | 62,500 | 16.9 | 2 |
| Anionic | Wet End | 175,000 | 11.0 | 3 |
|  | Pad Bath | 112,500 | 13.0 | 3 |

Under the conditions of the present test the cationic debonder was the most efficient class of material. Pad bath addition was more efficient for the nonionic and anionic debonders than wet end addition. This may be due to an incompatibility or zeta potential unbalance between the particular type or concentration of retention aid and debonder. It is expected that with additional experimentation similar results would be obtained for wet end and pad bath addition. The particular anionic system chosen for these samples was not particularly efficient.

EXAMPLE 12

Wet tensile strength is believed to be one measure of the ease of reslurrying a sheeted material. An additional set of samples was made in similar fashion to those of Example 9. Wet tensile strength was measured on specimens taken from the Noble and Wood handsheets. Measurements were made using horizontal specimens 100 mm wide and 80 mm between grips, with a head speed of ⅓ mm/sec. Values were as noted in Table XI.

TABLE XI

Wet Tensile Strength Values

| Treatment | Tensile Strength, kN/m |
|---|---|
| None | 8 |
| Crosslinked, no softener | 89 |
| Crosslinked, with softener | 30 |

The combination of softener with the crosslinked pulp reduced wet tensile strength to ⅓ of that without softener.

EXAMPLE 13

While some latent crosslinking reagents require additional heating at elevated temperatures after the sheet is normally dried, in order to effect reasonably complete reaction with the cellulose, others will react sufficiently under normal drying conditions. The use of urea nitrate as a catalyst for the urea-based latent crosslinking materials generally eliminates the need for post-drying heating. This material appears to be more active than the normally used inorganic salts or salt mixtures. Urea nitrate can be made with equimolar portions of urea and nitric acid under aqueous reaction conditions, using the method of Hebeish and Ibraham, *Textile Res Jour.*, 52 (2):116–122 (1982).

A series of samples was made following the procedure of Example 5. Arotex 900 DMDHEC latent crosslinker was used in pad bath percentages varying between 2.5% and 20% with urea nitrate present in the bath equivalent to 3.3% of the DMDHEC, as calculated on a dry materials basis. Samples for testing were dried to about 4% moisture content without any additional post drying heating. The sample temperatures probably did not exceed about 90° C. at any time. Bulk densities and air resistance values age given in the following table.

TABLE XII

Bulk Density and Air Resistance of Low Temperature Crosslinked Sheets

| As Received Crosslinker in Pad Bath, % | Crosslinker Solids Based on Pulp, % | Handsheet Bulk Density, cm³/g | Air Resistance Pressure Drop, mm |
|---|---|---|---|
| 0 | 0 | 3.0 | 47.2 |
| 2.5 | 1.0 | 6.3 | 17.8 |
| 5.0 | 1.9 | 10.0 | 13.2 |
| 10.0 | 3.8 | 15.4 | 3.1 |
| 15.0 | 5.7 | 20.5 | 1.8 |
| 20.0 | 7.6 | 22.5 | 1.5 |

Bulk and air resistance results are generally comparable with those reported in Table VI where a post drying reaction period of 1.5 minutes at 150° C. was used.

It will be apparent to those skilled in the art that many departures can be made from the present description and examples while remaining within the spirit of the invention. The invention is to be considered as being limited only by the following claims.

We claim:

1. A chemically crosslinked cellulosic product, comprising:
   unrefined cellulose fibers having a water content of at least about 10 percent prior to being crosslinked;
   a cationic debonding agent in an amount of from about 0.1 kg/ton to about 200 kg/ton of fiber; and
   a crosslinking agent with the fibers having a water content of greater than about ten percent in an amount from about 0.1 kg/ton to about 200 kg/ton and which is thereafter cured to crosslink the fibers.

2. The product according to claim 1 wherein the crosslinking agent is a polycarboxylic acid or is selected from the group of urea derivatives consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof.

3. The product according to claim 1 wherein the crosslinking agent was added in an amount of from about 0.1 to about 20 kg/ton of fiber.

4. The product according to claim 2 wherein the crosslinking agent was added in an amount of from about 1 kg/ton to about 10 kg/ton of fiber.

5. The product according to claim 1 wherein the debonding agent was added in an amount of from about 0.1 kg/ton to about 20.0 kg/ton of fiber.

6. The product according to claim 5 wherein the debonding agent was added in an amount of from about 1.0 kg/ton to about 10.0 kg/ton of fiber.

7. The product according to claim 1 wherein the debonding agent is a quaternary ammonium salt.

8. The product according to claim 1 wherein the debonding agent is selected from the group consisting of

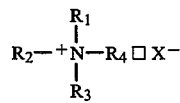 (1)

 (2)

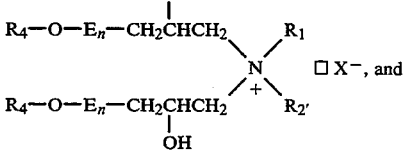 (3)

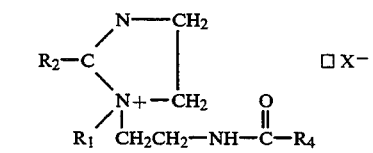 (4)

9. The product according to claim 1 and further including a cationic retention aid.

10. The product according to claim 1 wherein the crosslinking agent is dimethylol urea.

11. The product according to claim 1 wherein the crosslinking agent is dimethylol dihydroxyethyleneurea.

12. The product according to claim 1 wherein the crosslinking agent is dihydroxyethylene urea.

13. The product according to claim 1 wherein the crosslinking agent is dimethyldihydroxyethyleneurea.

14. The product according to claim 1 wherein the crosslinking agent is polycarboxylic acid.

15. The product according to claim 1 wherein the product has a bulk of greater than about 20 cm$^3$/g.

16. The product according to claim 1 wherein the polycarboxylic acid is 1,2,3,4-butanetetracarboxylic acid.

17. A chemically crosslinked cellulosic product, comprising:
    unrefined cellulose fibers having a moisture content of greater than about 30 percent before drying and crosslinking the product at a temperature of greater than about 100° C. for a period of from about 1 minute to about 5 minutes;
    a cationic debonding agent in an amount of about 0.1–20 kg/ton of fiber; and
    a water soluble or water dispersible latent cellulose crosslinking agent, wherein the crosslinking agent is a polycarboxylic acid or is selected from the group of urea derivatives consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof, the crosslinking agent being added in an amount of about 0.1–20 kg/ton of fiber.

18. The product according to claim 17 wherein the crosslinking agent is selected from the group of urea derivatives consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof, and the product further includes an effective amount of an acidic catalyst.

19. The product according to claim 17 wherein the cationic debonding agent is a quaternary ammonium salt.

20. The product according to claim 17 wherein the cationic debonding agent is selected from the group consisting of consisting of

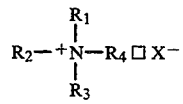 (1)

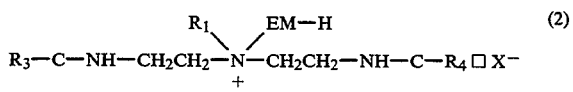 (2)

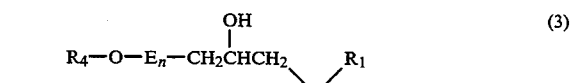

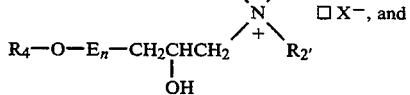 (3)

-continued

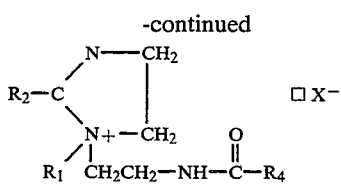

21. A cellulosic product comprising:
(1) a first, chemically crosslinked cellulosic fiber fraction comprising (a) unrefined cellulose fiber having a water content of greater than about 10 percent prior to being crosslinked; (b) a cationic debonding agent in an amount of from about 0.1 kg/ton to about 200 kg/ton of fiber; and (c) a water soluble or water dispersible latent cellulose crosslinking agent, wherein the crosslinking agent is a polycarboxylic acid or is selected from the group of urea derivatives consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof, the crosslinking agent being added in an amount of from about 0.1 kg/ton to about 200 kg/ton of fiber; and
(2) a second fiber fraction comprising conventional fiber furnish.

22. The product according to claim 21 wherein the first fiber fraction comprises from about 0.1 weight percent to about 60 weight percent of the total weight of the product.

23. A method of making a crosslinked cellulose product which comprises the steps of:
providing a sheet of wet, unrefined cellulose fibers having a moisture content greater than 30%;
providing within said fibers a debonding agent and a water soluble or water dispersible latent cellulose crosslinking agent, wherein the crosslinking agent is added to the cellulosic sheet in the wet press section of a paper machine, and wherein the crosslinking agent is a polycarboxylic acid or is selected from the group of urea derivatives consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof; and
immediately after providing the crosslinking agent, drying the fibers at an elevated temperature to simultaneously dry the fibers and dry crosslink the fibers with the crosslinking agent.

24. A method of making a crosslinked cellulose product which comprises the steps of:
providing wet, unrefined cellulose fibers having a moisture content greater than 30%;
providing within said fibers a debonding agent, in an amount of from about 1–10 kg/ton of cellulose fiber, and a water soluble or water dispersible latent cellulose crosslinking agent, wherein the crosslinking agent is a polycarboxylic acid or is selected from the group of urea derivatives consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof; and
immediately after providing the crosslinking agent, drying the fibers at an elevated temperature to simultaneously dry the fibers and dry crosslink the fibers with the crosslinking agent.

25. A method of making a crosslinked cellulose product which comprises the steps of:
providing wet, unrefined cellulose fibers having a moisture content greater than 30%;
providing within said fibers a debonding agent, in an amount of from about 20–200 kg/ton of cellulose fiber, and a water soluble or water dispersible latent cellulose crosslinking agent, wherein the crosslinking agent is a polycarboxylic acid or is selected from the group of urea derivative consisting of methylolated urea, methylolated cyclic ureas, methylolated lower alkyl substituted cyclic ureas, dihydroxy cyclic ureas, lower alkyl substituted dihydroxy cyclic ureas, and methylolated dihydroxy cyclic ureas; and mixtures thereof, wherein the crosslinking agent is added in an amount of about 2–200 kg/ton of fiber; and
immediately after providing the crosslinking agent, drying the fibers at an elevated temperature to simultaneously dry the fibers and dry crosslink the fibers with the crosslinking agent.

* * * * *